(12) United States Patent
Taylor et al.

(10) Patent No.: US 7,731,757 B2
(45) Date of Patent: Jun. 8, 2010

(54) OBESITY TREATMENT

(75) Inventors: Thomas V. Taylor, Houston, TX (US); Frank G. Weeden, Houston, TX (US)

(73) Assignee: Reflux Corporation, Houston, TX (US)

( * ) Notice: Subject to any disclaimer, the term of this patent is extended or adjusted under 35 U.S.C. 154(b) by 1531 days.

(21) Appl. No.: 10/709,828

(22) Filed: Jun. 1, 2004

(65) Prior Publication Data
US 2004/0243152 A1 Dec. 2, 2004

Related U.S. Application Data

(60) Provisional application No. 60/320,241, filed on Jun. 1, 2003.

(51) Int. Cl.
*A61F 2/04* (2006.01)
(52) U.S. Cl. .................................. 623/23.64
(58) Field of Classification Search ... 623/23.64–23.65; 606/151
See application file for complete search history.

(56) References Cited

U.S. PATENT DOCUMENTS

| | | | |
|---|---|---|---|
| 3,574,865 A | 4/1971 | Hamaker | |
| 4,056,854 A | 11/1977 | Boretos et al. | |
| 4,133,315 A | 1/1979 | Berman et al. | 128/303 R |
| 4,265,694 A | 5/1981 | Boretos et al. | |
| 4,485,805 A | 12/1984 | Foster, Jr. | 128/1 R |
| 4,501,264 A | 2/1985 | Rockey | 128/1 R |
| 4,607,618 A | 8/1986 | Angelchik | 128/1 R |
| 4,723,547 A | 2/1988 | Kullas et al. | 128/329 R |
| 4,844,068 A * | 7/1989 | Arata et al. | 227/175.1 |
| 4,846,836 A | 7/1989 | Reich | |
| 4,899,747 A | 2/1990 | Garren et al. | 606/192 |
| 4,921,484 A | 5/1990 | Hillstead | 604/104 |
| 4,957,508 A | 9/1990 | Kaneko et al. | |
| 4,994,071 A | 2/1991 | MacGregor | 606/194 |

(Continued)

FOREIGN PATENT DOCUMENTS

EP 0857471 8/1998

(Continued)

OTHER PUBLICATIONS

Dua, Kulwinder S. MD et al, "Self Expanding Metal Esophageal Stent with Anti-Reflux Mechanism," Gastrointestinal Endoscopy, vol. 53, No. 6, p. 603 (2001).

(Continued)

*Primary Examiner*—Julian W Woo
*Assistant Examiner*—Gregory Anderson
(74) *Attorney, Agent, or Firm*—Daniel N. Lundeen; Lundeen & Lundeen, PLLC

(57) ABSTRACT

A food intake-limiting device for peroral implantation in the stomach adjacent a gastroesophageal junction is disclosed. The device can have an inner basket nested in an outer basket, a proximal entry opening and a distal exit opening to limit a rate of efflux, mesh openings in the outer basket for protrusion of stomach lining into the outer basket, and a plurality of spikes mounted tangentially on the inner basket for transfixing the protruding stomach lining. The inner basket is rotatable with respect to the outer basket to effect the transfixation. Also disclosed are an implantation/extraction tool, and methods for implanting and removing the device in a patient in need of obesity treatment.

19 Claims, 8 Drawing Sheets

U.S. PATENT DOCUMENTS

| | | | |
|---|---|---|---|
| 5,006,106 A | 4/1991 | Angelchik | |
| 5,163,953 A | 11/1992 | Vince | |
| 5,314,473 A | 5/1994 | Godin | |
| 5,382,231 A | 1/1995 | Shlain | 604/49 |
| 5,411,552 A | 5/1995 | Andersen et al. | |
| 5,618,299 A * | 4/1997 | Khosravi et al. | 623/1.2 |
| 5,695,504 A * | 12/1997 | Gifford et al. | 606/153 |
| 5,855,601 A | 1/1999 | Bessler et al. | |
| 5,861,036 A | 1/1999 | Godin | |
| 5,868,141 A | 2/1999 | Ellias | 128/898 |
| 5,871,536 A | 2/1999 | Lazarus | |
| 5,873,904 A | 2/1999 | Ragheb et al. | |
| 5,876,448 A | 3/1999 | Thompson et al. | |
| 5,922,019 A | 7/1999 | Hankh et al. | |
| 6,254,642 B1 | 7/2001 | Taylor | |
| 6,287,334 B1 | 9/2001 | Moll et al. | |
| 6,544,291 B2 | 4/2003 | Taylor | |
| 6,558,429 B2 | 5/2003 | Taylor | |
| 6,666,873 B1 * | 12/2003 | Cassell | 606/153 |
| 6,958,079 B1 | 10/2005 | Taylor | |
| 2001/0020189 A1 * | 9/2001 | Taylor | 623/23.68 |
| 2001/0020190 A1 | 9/2001 | Taylor | |
| 2003/0040772 A1 * | 2/2003 | Hyodoh et al. | 606/200 |
| 2003/0060894 A1 * | 3/2003 | Dua et al. | 623/23.68 |
| 2004/0148034 A1 * | 7/2004 | Kagan et al. | 623/23.65 |
| 2005/0177181 A1 * | 8/2005 | Kagan et al. | 606/151 |

FOREIGN PATENT DOCUMENTS

| | | |
|---|---|---|
| WO | 9629954 | 10/1996 |

OTHER PUBLICATIONS

Valbuena Jose, MD, "Palliation of Gastroesophageal Carcinoma with Endoscopic Insertion of a New Antireflux Prosthesis," Gastrointestinal Endoscopy, vol. 30, No. 4, p. 241 (1984).

Nunes, Carlos C., et al, "Comparative Post-operative Study of Prostheses, with and without an Anti-Reflux Valve System, In the Palliative Treatment of Esophageal Carcinoma," Hepato-Gastroenterology, Vo. 46, pp. 2859-2864 (1999).

* cited by examiner

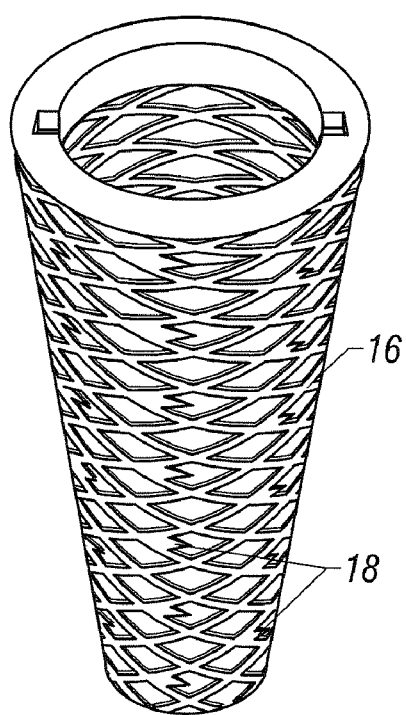
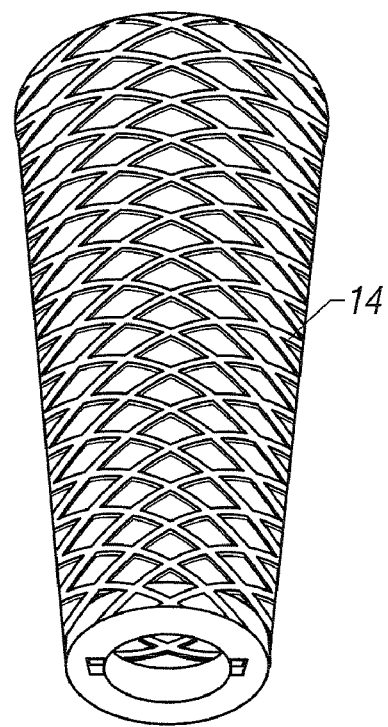
FIG. 4A          FIG. 4B
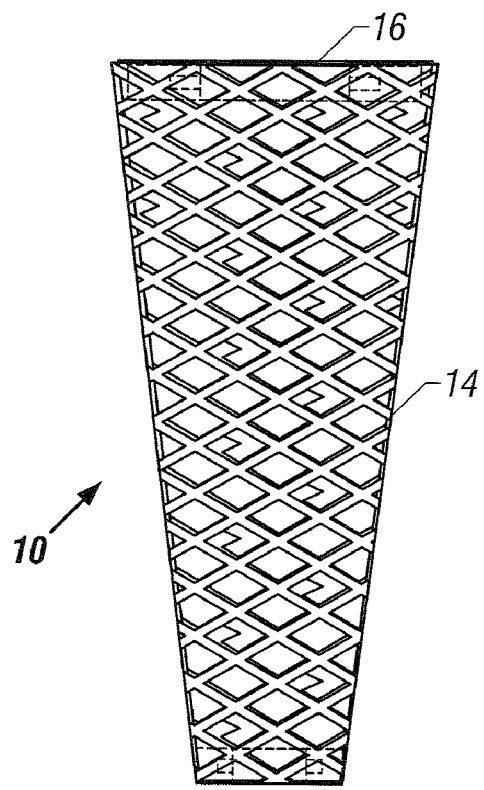
FIG. 5

OBESITY TREATMENT

CROSS REFERENCE TO RELATED APPLICATIONS

This application claims the benefit of our provisional application U.S. Ser. No. 60/320,241, filed Jun. 1, 2003.

BACKGROUND OF INVENTION

The present invention relates to the treatment of obesity, and more particularly to a gastric restriction device and an implantation tool, system and method for peroral implantation and removal thereof.

In the prior art, one method of treating severe obesity is to perform a surgery in which a row of staples S and a ring R are placed in or on the stomach to form a pouch A as seen in FIGS. 1-2. The staples S extend downwardly from adjacent the esophageal junction from the top of the stomach to the ring R to form one side of the pouch A. The ring R restricts the passage of food from the pouch A. The food exiting the esophagus enters the pouch A and, as it is digested by the stomach acids that can enter the pouch A, enters the main volume B of the stomach in a delayed manner through the ring R. This prevents the patient from eating too much food at one time, and is very effective in inducing weight loss. However, the surgery requires opening the abdominal cavity, an extended hospital stay and a risk of surgical complications.

SUMMARY OF INVENTION

The present invention provides a perorally implantable and retrievable gastric restriction device. In one embodiment, the invention provides a food intake-limiting device for peroral implantation in the stomach adjacent a gastroesophageal junction. The device includes inner and outer elements defining an ingestion chamber with a proximal entry opening and a distal exit opening to limit a rate of efflux. A plurality of openings are formed in the outer element for protrusion of stomach lining to the inner element. The inner element includes a plurality of retention members to hold the protruding stomach lining, whereby the device is secured to the stomach lining.

The inner and outer elements can be nested baskets. The openings in the outer element can be formed by a mesh in the outer element. The retention elements can be tangential spikes. The inner and outer elements are preferably rotatable with respect to each other to actuate the retention members. The retention members are preferably releasable. The device can include a distal end ring in the outer element, and a proximal end ring in the inner element. The inner and outer elements can be frustoconically tapered from a relatively larger proximal radius to a relatively smaller distal radius. The inner element can have mesh openings, and the retention members can have spikes tangentially oriented in a plurality of the mesh openings.

In another embodiment, the invention provides a device having an inner basket nested in an outer basket, a proximal entry opening and a distal exit opening to limit a rate of efflux, a mesh structure in the outer basket, and a plurality of spikes mounted tangentially on the inner basket adjacent mesh openings in the outer basket. The inner basket is rotatable with respect to the outer basket between a release position comprising a gap between points of the spikes and mesh elements of the outer basket and a second position comprising an overlap between the points of the spikes and the mesh elements. The device can further include a distal end ring in the outer basket, and a proximal end ring in the inner basket. The inner and outer baskets can be frustoconically tapered from a relatively larger proximal radius to a relatively smaller distal radius. The inner basket can have mesh openings and the spikes are preferably tangentially oriented in a plurality of the mesh openings.

In another embodiment, the present invention provides a food intake-limiting device for peroral implantation in the stomach adjacent a gastroesophageal junction. The device has an inner basket nested in an outer basket, a proximal entry opening and a distal exit opening to limit a rate of efflux, mesh openings in the outer basket for protrusion of stomach lining into the outer basket, and a plurality of spikes mounted tangentially on the inner basket for transfixing the protruding stomach lining. The inner basket is rotatable with respect to the outer basket to effect the transfixation.

The invention also provides a tool for peroral manipulation of the devices described above in the stomach adjacent the esophageal junction. The tool includes, in combination therewith, an inner tube slideably and rotatably received in an outer tube, a hub on a distal end of each of the inner and outer tubes for releasably engaging a respective end ring of the outer and inner baskets, a handle on a proximal end of each of the inner and outer tubes, and a connector for placing a vacuum or pressure source in fluid communication with perforations in the inner tube adjacent the distal end thereof.

The invention also provides a method for peroral implantation of the intake-restricting devices in a stomach of a patient adjacent a gastroesophageal junction using the manipulation tool. The method includes (a) securing the distal hub of the inner tube in the end ring of the outer basket, (b) securing the distal hub of the outer tube in the end ring of the inner basket, (c) inserting the inner and outer baskets through the mouth and esophagus of the patient and positioning them below the esophageal junction, (d) applying vacuum to the connector to draw stomach lining into the mesh openings of the outer basket, (e) manipulating the proximal handles to rotate the inner basket with respect to the outer basket, transfix stomach lining protruding into the mesh openings and fix the baskets in place, (f) terminating the vacuum application, (g) disengaging the distal hub of the inner tube from the end ring of the outer basket, (h) disengaging the distal hub of the outer tube from the end ring of the inner basket, and (i) withdrawing the tool.

The invention further provides a method for peroral extraction of the intake-restricting device implanted in a stomach adjacent a gastroesophageal junction of a patient using the manipulation tool. The method includes (a) inserting a distal end of the tool through the mouth and esophagus of the patient, (b) securing the distal hub of the inner tube in the end ring of the outer basket, (c) securing the distal hub of the outer tube in the end ring of the inner basket, (d) manipulating the proximal handles to rotate the inner basket with respect to the outer basket and open a gap between each point of the spikes and the adjacent mesh member, (e) applying pressure to the connector to disengage stomach lining from the spikes and the mesh openings of the outer basket, and (f) removing the inner and outer baskets through the esophagus and mouth of the patient.

BRIEF DESCRIPTION OF DRAWINGS

FIG. 4A is a perspective view of an outer basket according to one embodiment of the invention.

FIG. 4B is a perspective view of an inner basket according to one embodiment of the invention.

FIG. 5 is a side view of the inner basket of FIG. 4B nested in the outer basket of FIG. 4A according to one embodiment of the invention.

DETAILED DESCRIPTION

Figure 1A:
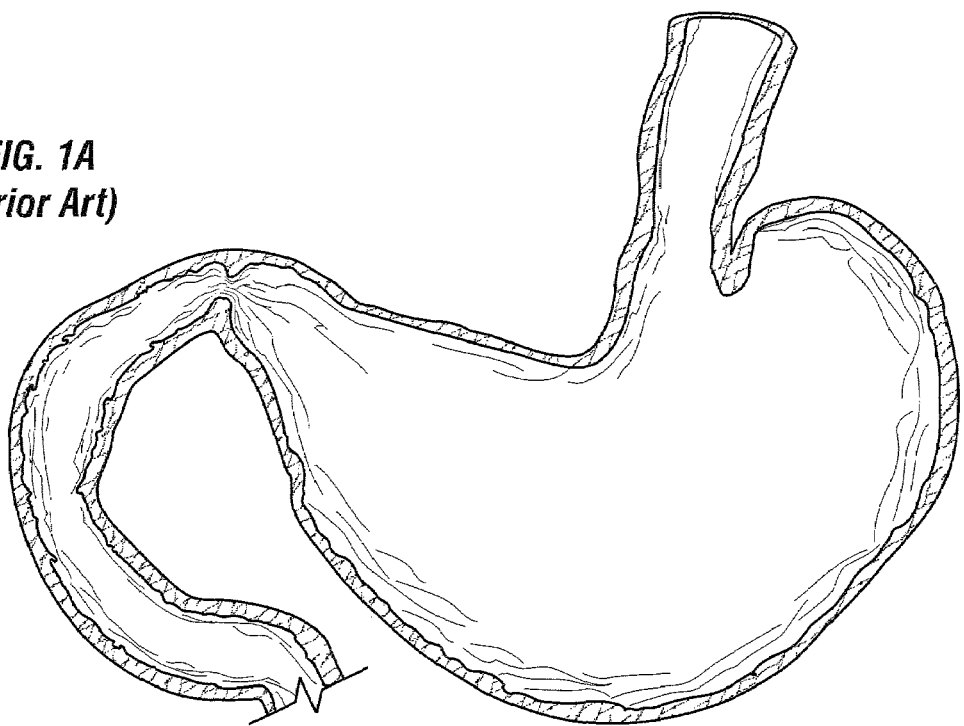
FIG. 1A generally shows a stomach and the gastroesophageal junction.
Figure 1B:
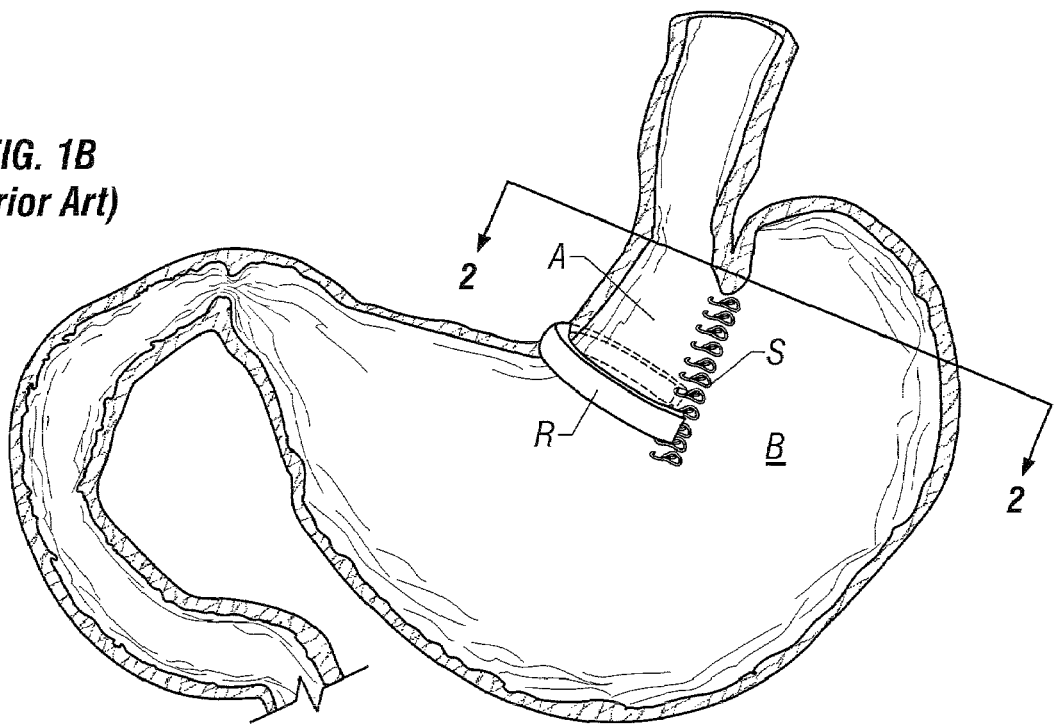
FIG. 1B shows a prior art stapling procedure in the stomach of FIG. 1A.
Figure 2:
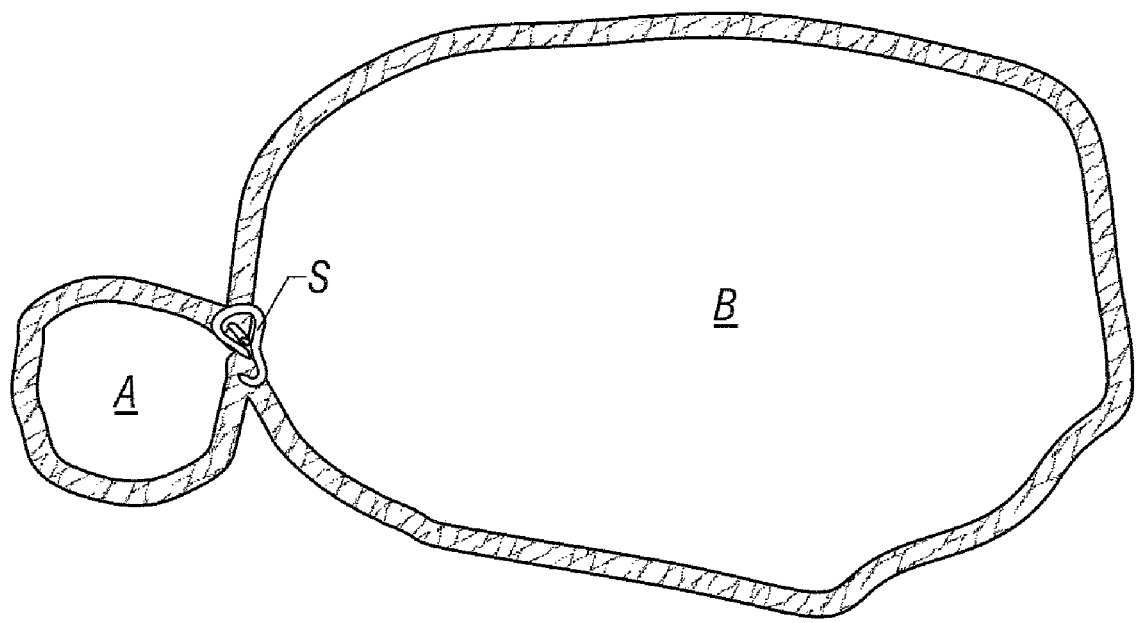
FIG. 2 is a cross sectional view of the stapling as seen along the lines 2-2 of FIG. 1B.
Figure 3A:
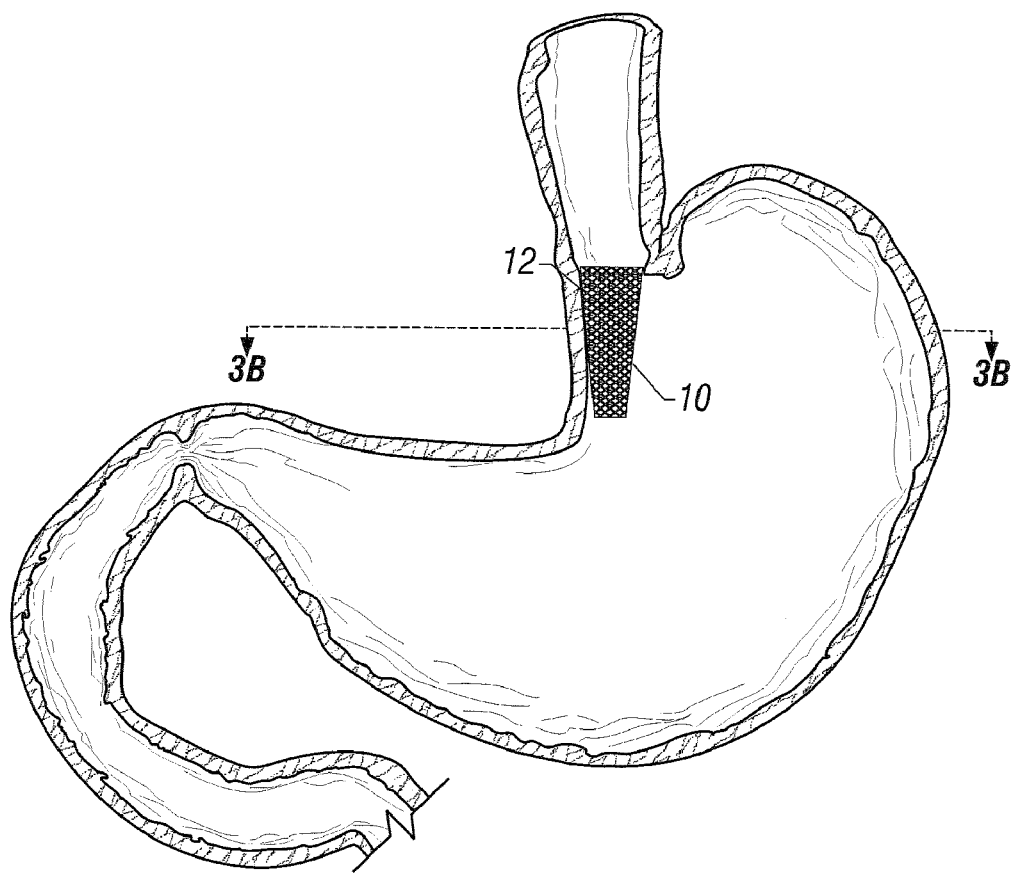
FIG. 3A shows a gastric restriction device implanted in the stomach according to one embodiment of the present invention.
Figure 3B:
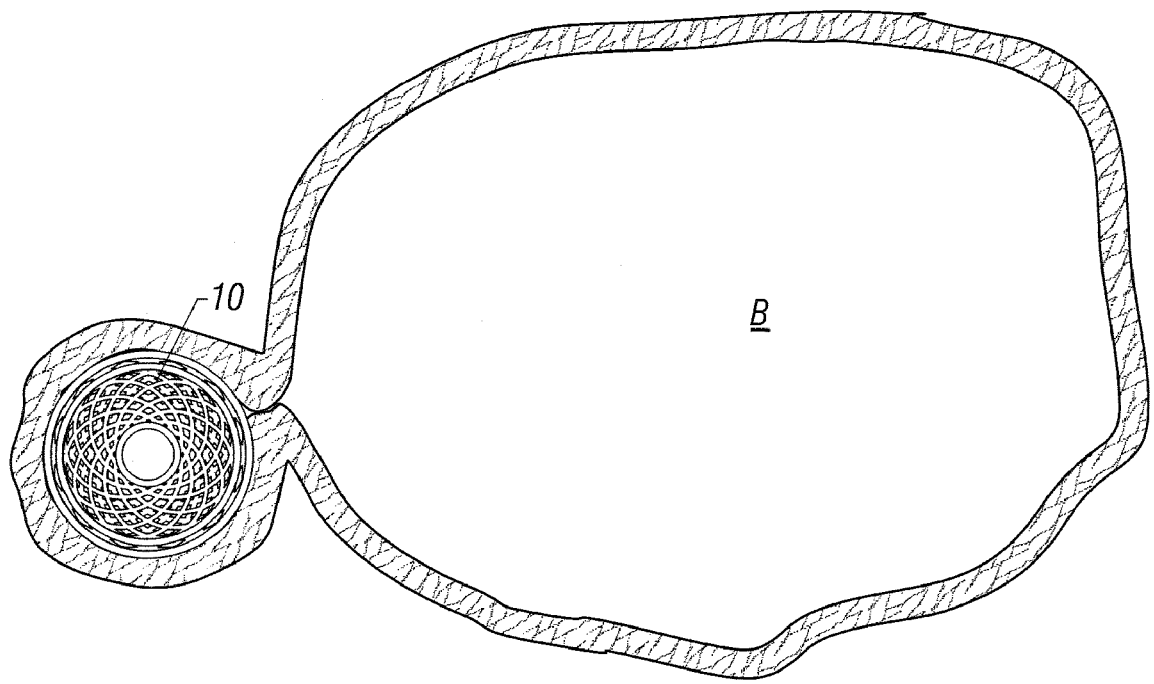
FIG. 3B is a cross sectional view of the implant as seen along the lines 3B-3B of FIG. 3A.

In one example of the present invention, the gastric restriction "pouch" is formed by endoscopically inserting a device 10 comprising a pair of concentric baskets that are attached to the lining of the stomach 12, as best seen in FIG. 3. The device 10 functions by forming a gastric antechamber at the gastroesophageal junction that limits the volume of food that can be eaten at one time, in much the same manner as the prior art stomach stapling procedure. The openings in the side walls of the device 10 allow stomach acid to digest the food in the antechamber so that it is slowly released via an opening in the lower end into the main stomach volume. The patient cannot eat again until the antechamber empties.

As shown in FIGS. 4A, 4B and 5, the device 10 comprises concentric frustoconical outer basket 14 and corresponding inner basket 16 nested therein. The baskets 14, 16 are formed of an open mesh of a biologically inert material such as a metal and/or polymer, or polymer-coated metal, and can be rigid or somewhat flexible as long as they are not collapsed during the implantation described below. The baskets 14, 16 have a distal end with a smaller opening and a proximal end with a relatively larger opening. The device 10 preferably has a volume of about 30 ml, for example, measuring 4 inches long with a 0.625-in. distal end diameter and a 1.25-in. proximal end diameter.

The inner basket 16 has a plurality of preferably tangentially oriented spikes 18 that transfix the stomach lining that protrudes through the mesh openings in the outer basket 14. The spikes 18 are preferably evenly spaced throughout the mesh openings in the inner basket 16, e.g. every other mesh opening. The spikes 18 preferably extend from one corner or apex of a mesh opening toward the opposite corner, but with a gap between the point of the spike 18 and the opposite corner of the same mesh opening in the inner basket 16. However, the mesh openings of the outer basket 14, which preferably have the same size and longitudinal orientation as those of the inner basket 16, are radially offset from the mesh openings in the inner basket 16 such that the free end of the spikes 18 lies beneath the wire of the outer basket 14. This inhibits the transfixed stomach lining from working free from the spikes 18. In this manner, the inner basket 16 and the outer basket 14 are firmly secured in nested relationship in place in the stomach 12.

Figure 6A:
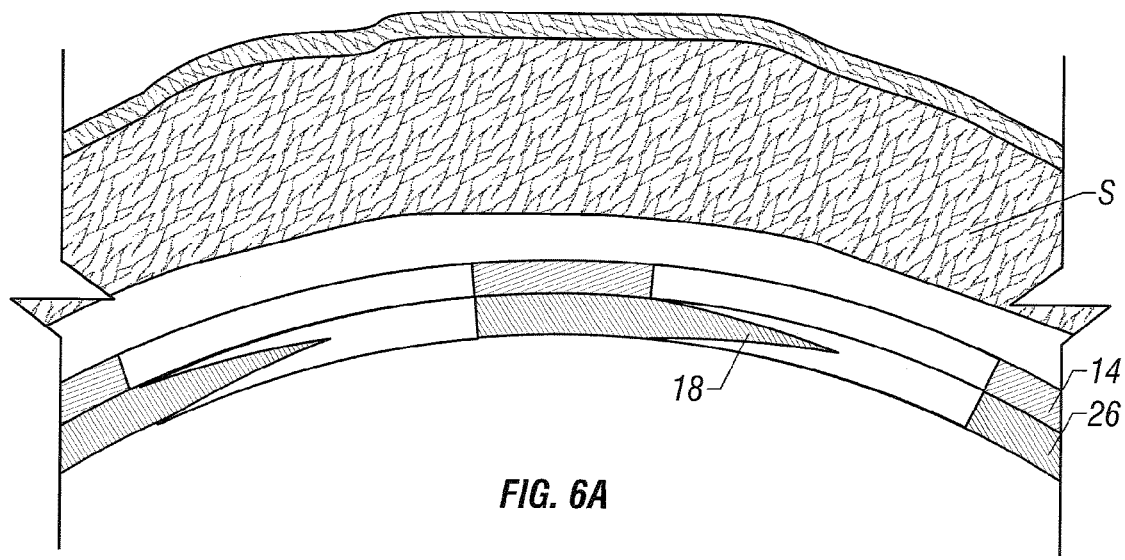
FIG. 6A is a sectional plan view of the nested baskets of FIG. 5 in the release or pre-implantation configuration adjacent to stomach lining.
Figure 6B:
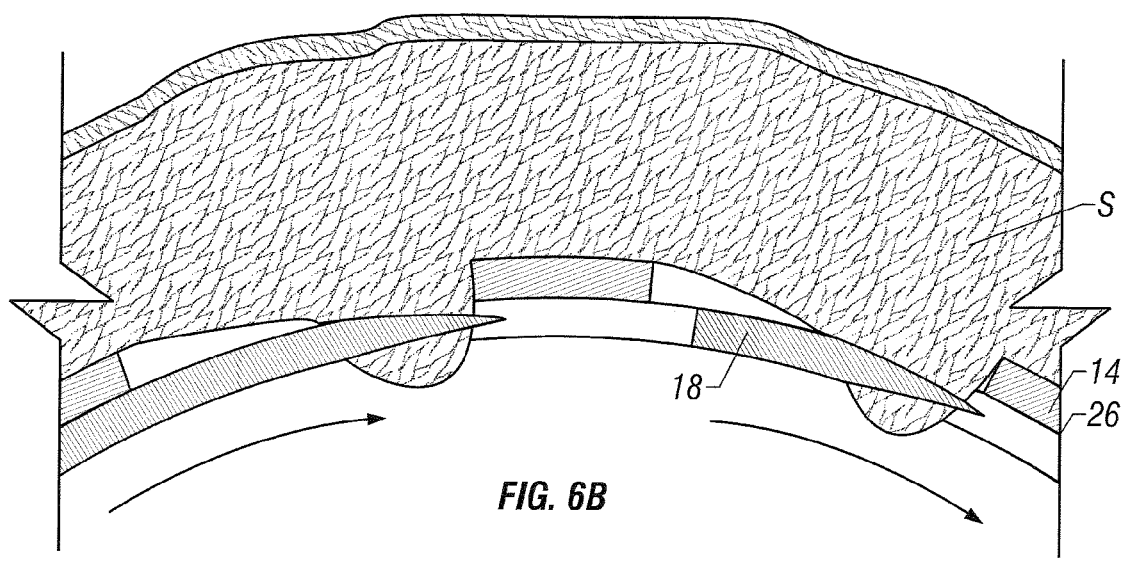
FIG. 6B is a sectional plan view of the nested baskets of FIG. 5 during implantation adjacent to stomach lining.

The baskets 14, 16 can be positioned in the stomach just below the esophageal junction using an endoscopic tool described in more detail below. During insertion, the mesh openings of the outer basket 14 are aligned with those of the inner basket 16 so that there is a gap between the point of the spikes 18 and the opposite mesh corner, as shown in FIG. 6A. Once the baskets 14, 16 are positioned in the stomach 12 as desired, a vacuum source is applied to the stomach via the endoscopic tool to draw the stomach lining S into the mesh openings in the baskets 14, 16. The inner basket 16 is then rotated with respect to the outer basket 14, e.g. 5 degrees, to the position shown in FIG. 6B. The rotation of the inner basket 16 causes the spikes 18 to pierce the stomach lining intrusions and close the gap between the free end of the spikes 18 and the mesh junction in the outer basket 14. Thus, the baskets are securely affixed to the stomach lining and secured in place. The endoscopic tool is released from the baskets 14, 16 and withdrawn, leaving the baskets 14, 16 in place in the stomach 12.

A desirable feature of the present invention is that the baskets 14, 16 can also be removed endoscopically by reversing the implantation procedure. The endoscopic tool is inserted to engage the baskets 14, 16 and rotate the inner basket 16 to align the meshes in the baskets 14, 16, as in FIGS. 5 and 6A, and open up a gap between the filaments of the mesh and the point of the spikes 18. Air can be introduced into the stomach 12 via the endoscopic tool to facilitate disengagement of the transfixed stomach lining from the spikes 18. The baskets 14, 16 can then be removed perorally without surgical intervention.

Figure 7A:
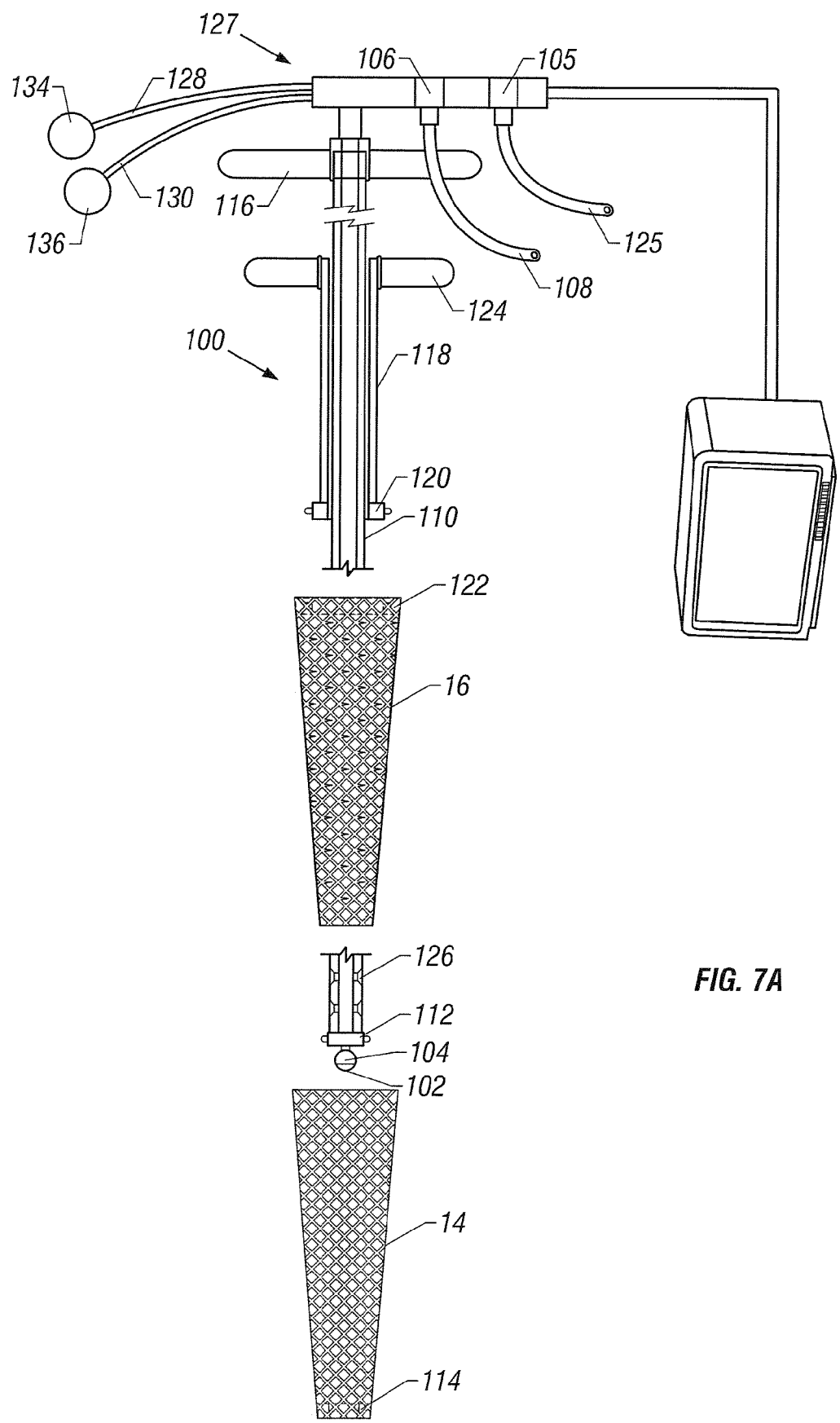
FIG. 7A is an exploded schematic of a manipulation tool according to one embodiment of the invention.

The implantation tool 100 shown in FIG. 7A comprises an endoscopic device with a distal camera 102, light source 104, vacuum connection 106 to vacuum line 108 and pressure connection 105 to pressurized gas line 125. An inner tube 110 is connected to a first distal hub 112, which releasably engages an end ring 114 in the distal end of the outer basket 14, and has a proximal handle 116 for rotating or holding the inner tube 110 (and outer basket 14). An outer tube 118 is connected to a second distal hub 120, which releasably engages end ring 122 in the proximal end of inner basket 16, and likewise has a proximal handle 124 for rotating the outer tube 118 (and inner basket 16). The vacuum source 106 is in communication with the annulus between the basket 16 and the inner tube 110, e.g. via perforations 126 in the inner tube 110 adjacent distal hub 112.

Figure 7B:
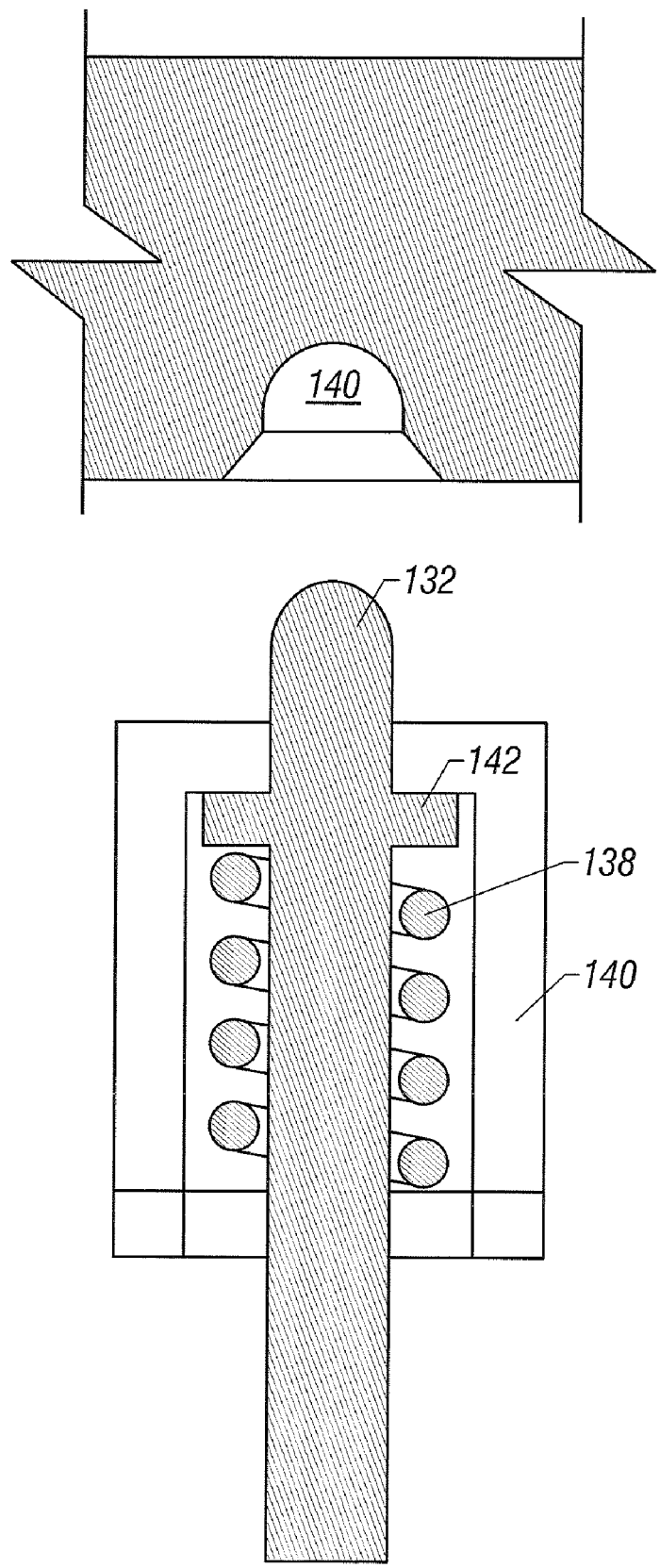
FIG. 7B is a sectional view of a basket retention element according to one embodiment of the invention.

Basket 14, 16 release means 127 can include cables 128, 130 in the respective tubes 110, 118 attached to respective spring-biased pins in the hubs 112, 120 and manipulation handles or pulls 134, 136 at the proximal end of the tool 100. As best seen in FIG. 7B, in one embodiment the release means 127 include pin 132 and spring 138 in a radially oriented housing 140. A shoulder 142 limits movement of the pin 132 and serves to compress the spring 138 for outwardly biasing the pin 132. The end of the pin 132 is removably received in a hole 140 formed in an inside surface of the end rings 114, 122. Preferably, the end of the pin 132 is rounded and the opening of the hole 140 is chamfered to facilitate engagement and disengagement of the hubs 112, 120 in and from the end rings 114, 122.

Figure 8:
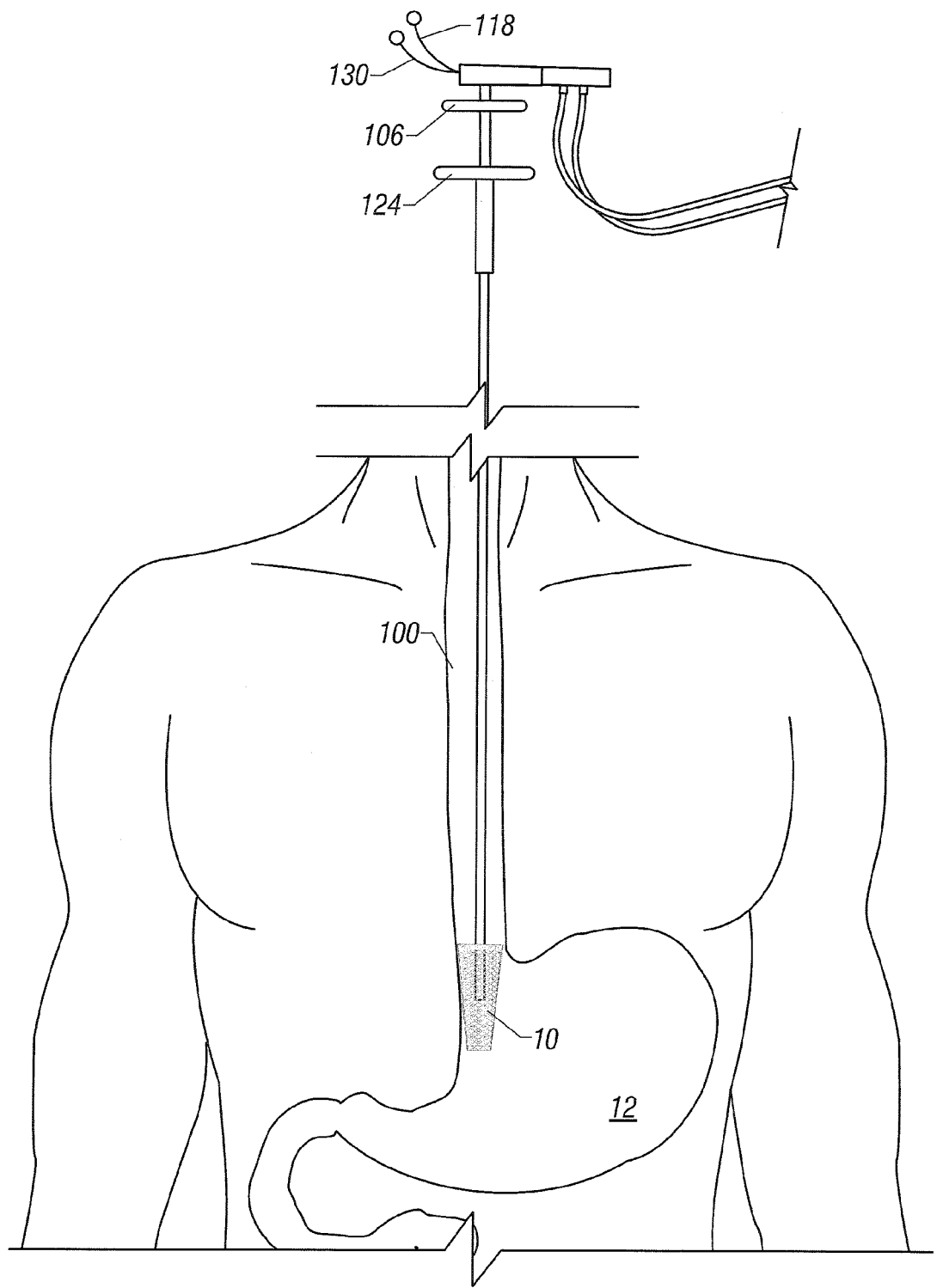
FIG. 8 is a schematic view of the manipulation tool being used in a patient in combination with the gastric restriction device according to one embodiment of the invention.

The present invention thus allows the implantation of a stomach intake-restriction device without surgery, as shown in FIG. 8. If desired, the tool 100 can also be used to endoscopically remove the baskets 14, 16 by reversing the implantation procedure, using stomach inflation with air to assist in releasing the stomach lining after reversing rotation of the baskets 14, 16.

The invention claimed is:

1. A food intake-limiting device for peroral implantation in the stomach adjacent a gastroesophageal junction, comprising:
    inner and outer elements defining an ingestion chamber with a proximal entry opening and a distal exit opening to limit a rate of efflux;
    a plurality of openings in the outer element for protrusion of stomach lining to the inner element;
    wherein the inner element includes a plurality of retention members to hold the protruding stomach lining, wherein the retention members comprise tangential spikes, whereby the device is secured to the stomach lining; and
    wherein the inner and outer elements are frustoconically tapered from a relatively larger proximal radius to a relatively smaller distal radius.

2. The device of claim 1 wherein the inner and outer elements comprise nested baskets.

3. The device of claim 1 wherein the openings are formed by a mesh in the outer element.

4. The device of claim 1 wherein the inner and outer elements are rotatable with respect to each other to actuate the retention members.

5. The device of claim 1 wherein the retention members are releasable.

6. The device of claim 1 comprising a distal end ring in the outer element, and a proximal end ring in the inner element.

7. The device of claim 1 wherein the inner element comprises mesh openings and the spikes are tangentially oriented in a plurality of the mesh openings.

8. A food intake-limiting device for peroral implantation in the stomach adjacent a gastroesophageal junction, comprising:
    an inner basket nested in an outer basket, further comprising a distal end ring in the outer basket and a proximal end ring in the inner basket;
    a proximal entry opening and a distal exit opening to limit a rate of efflux;
    a mesh structure in the outer basket;
    a plurality of spikes mounted tangentially on the inner basket adjacent mesh openings in the outer basket, wherein the inner basket is rotatable with respect to the outer basket between a release position comprising a gap between points of the spikes and mesh elements of the outer basket and a second position comprising an overlap between the points of the spikes and the mesh elements; and
    wherein the inner and outer baskets are frustoconically tapered from a relatively larger proximal radius to a relatively smaller distal radius.

9. The device of claim 8 wherein the inner basket has mesh openings and the spikes are tangentially oriented in a plurality of the mesh openings.

10. A food intake-limiting device for peroral implantation in the stomach adjacent a gastroesophageal junction, comprising:
    an inner element nested in an outer element, wherein the inner and outer elements are frustoconically tapered from a relatively larger proximal radius to a relatively smaller distal radius;
    a proximal entry opening and a distal exit opening to limit a rate of efflux;
    mesh openings in the outer element for protrusion of stomach lining into the outer element;
    a plurality of spikes mounted tangentially on the inner element for transfixing the protruding stomach lining, wherein the inner element is rotatable with respect to the outer element to effect the transfixation.

11. A tool for peroral manipulation of the device of claim 9 in the stomach adjacent the esophageal junction, comprising in combination therewith an inner tube slideably and rotatably received in an outer tube, a hub on a distal end of each of the inner and outer tubes for releasably engaging a respective end ring of the outer and inner baskets, a handle on a proximal end of each of the inner and outer tubes, and a connector for placing a vacuum or pressure source in fluid communication with perforations in the inner tube adjacent the distal end thereof.

12. A method for peroral implantation of an intake-restricting device in a stomach of a patient adjacent a gastroesophageal junction using the tool of claim 11, comprising the steps of securing the distal hub of the inner tube in the end ring of the outer basket, securing the distal hub of the outer tube in the end ring of the inner basket, inserting the inner and outer baskets through the mouth and esophagus of the patient and positioning them below the esophageal junction, applying vacuum to the connector to draw stomach lining into the mesh openings of the outer basket, manipulating the proximal handles to rotate the inner basket with respect to the outer basket, transfix stomach lining protruding into the mesh openings and fix the baskets in place, terminating the vacuum application, disengaging the distal hub of the inner tube from the end ring of the outer basket, disengaging the distal hub of the outer tube from the end ring of the inner basket, and withdrawing the tool.

13. A method for peroral extraction of the intake-restricting device implanted in a stomach adjacent a gastroesophageal junction of a patient using the tool of claim 11, comprising the steps of inserting a distal end of the tool through the mouth and esophagus of the patient, securing the distal hub of the inner tube in the end ring of the outer basket, securing the distal hub of the outer tube in the end ring of the inner basket, manipulating the proximal handles to rotate the inner basket with respect to the outer basket and open a gap between each point of the spikes and the adjacent mesh member, applying pressure to the connector to disengage stomach lining from the spikes and the mesh openings of the outer basket, and removing the inner and outer baskets through the esophagus and mouth of the patient.

14. The device of claim 8 comprising a distal end ring in the outer basket, and a proximal end ring in the inner basket.

15. A method for peroral implantation of an intake-restricting device in a stomach of a patient adjacent a gastroesophageal junction, wherein the intake-restricting device comprises inner and outer elements defining an ingestion chamber with a proximal entry opening and a distal exit opening to limit a rate of efflux, a plurality of openings in the outer element for protrusion of stomach lining to the inner element, wherein the inner element includes a plurality of retention members to hold the protruding stomach lining, wherein the inner and outer elements are rotatable with respect to each other to actuate the retention members, whereby the device is secured to the stomach lining, and wherein the inner and outer elements are frustoconically tapered from a relatively larger proximal radius to a relatively smaller distal radius, comprising the steps of:
    providing a manipulation tool, comprising:
        an inner tube slideably and rotatably received in an outer tube;

a hub on a distal end of each of the inner and outer tubes for releasably engaging a respective distal end of the outer element and a proximal end of the inner element;

a handle on a proximal end of each of the inner and outer tubes; and a connector for placing a vacuum source in fluid communication with perforations in the inner tube adjacent the distal end thereof securing the distal hub of the inner tube in the distal end of the outer element;

securing the distal hub of the outer tube in the proximal end of the inner element;

inserting the inner and outer elements through the mouth and esophagus of the patient and positioning them below the esophageal junction;

applying vacuum to the connector to draw stomach lining into the plurality of openings in the outer element;

manipulating the proximal handles to rotate the inner element with respect to the outer element to actuate the retention members to hold the stomach lining protruding into the plurality of openings and fix the inner and outer elements in place;

terminating the vacuum application;

disengaging the distal hub of the inner tube from the distal end of the outer element;

disengaging the distal hub of the outer tube from the proximal end of the inner element; and withdrawing the tool.

16. The method of claim 15 wherein the retention elements comprise tangential spikes.

17. The method of claim 15 wherein the inner and outer elements comprise nested baskets and wherein the openings are formed by a mesh in the outer basket.

18. The method of claim 15 comprising a distal end ring in the outer element, and a proximal end ring in the inner element.

19. A method for peroral extraction of an intake-restricting device implanted in a stomach adjacent a gastroesophageal junction of a patient, wherein the intake-restricting device comprises inner and outer elements defining an ingestion chamber with a proximal entry opening and a distal exit opening to limit a rate of efflux, a plurality of openings in the outer element for protrusion of stomach lining to the inner element, wherein the inner element includes a plurality of retention members to hold the protruding stomach lining, wherein the inner and outer elements are rotatable with respect to each other to actuate the retention members, whereby the device is secured to the stomach lining, and wherein the inner and outer elements are frustoconically tapered from a relatively larger proximal radius to a relatively smaller distal radius, comprising the steps of:

inserting a distal end of a manipulation tool through the mouth and esophagus of the patient, wherein the manipulation tool comprises:

an inner tube slideably and rotatably received in an outer tube;

a hub on a distal end of each of the inner and outer tubes for releasably engaging a respective distal end of the outer element and a proximal end of the inner element;

a handle on a proximal end of each of the inner and outer tubes; and a connector for placing a pressure source in fluid communication with perforations in the inner tube adjacent the distal end thereof;

securing the distal hub of the inner tube in the distal end of the outer element;

securing the distal hub of the outer tube in the proximal end of the inner element;

manipulating the proximal handles to rotate the inner element with respect to the outer element to release the retention members;

applying pressure to the connector to disengage stomach lining from the retention members and the plurality of openings in the outer element; and removing the inner and outer elements through the esophagus and mouth of the patient.

* * * * *